United States Patent [19]

Higa et al.

[11] Patent Number: 4,731,377

[45] Date of Patent: Mar. 15, 1988

[54] ANTITUMOR CYCLIC PEROXIDES

[75] Inventors: Tatsuo Higa, Okinawa, Japan; Carsten Christophersen, Copenhagen, Denmark; Shinichi Sakemi, Vero Beach, Fla.

[73] Assignee: Harbor Branch Oceanographic Institute, Inc., Ft. Pierce, Fla.

[21] Appl. No.: 825,061

[22] Filed: Jan. 31, 1986

[51] Int. Cl.$^4$ .................... A61K 31/35; C07D 319/02
[52] U.S. Cl. .................................... 514/452; 549/357
[58] Field of Search ........................ 549/357; 514/452

[56] References Cited
PUBLICATIONS

Faulkner et al., C.A., 95, 21538h, (1981).
Faulkner et al., Colloq. Int. C.N.R.S., 1979, 291, (Biol. Spongiaires), 401-6.
Wells, Tetrahedron Letters, No. 33, pp. 2637-2638, (1976).
Higgs et al., J. Org. Chem., 43, 3454, (1978).
Ravi et al., ibid., 44, 3099, (1979).
Stierle et al., ibid., 45, 3396, (1980).
Phillipson et al., JACS, 105, 7735, (1983).

Primary Examiner—Nicky Chan
Attorney, Agent, or Firm—Carroll F. Palmer

[57] ABSTRACT

This invention relates to cyclic peroxide compositions, a process of producing the compositioning and a method for inhibiting tumors utilizing the compositions. More particularly, the compositions are cyclic peroxides which are derived from marine organisms, i.e., the marine sponge *Plakortis lita*.

7 Claims, No Drawings

ANTITUMOR CYCLIC PEROXIDES

FIELD OF THE INVENTION

This invention relates to new cyclic organic compounds which have useful antitumor activity. More particularly, this invention relates to new cyclic peroxides and cyclic peroxide antitumor compositions derived from marine organisms, i.e., marine sponge, *Plakortis lita*, and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors new methods and antitumor chemical compositions are needed.

Marine organisms and particularly marine sponges are a potential source for novel compositions. A cyclic peroxide, Chondrillin, having the following formula:

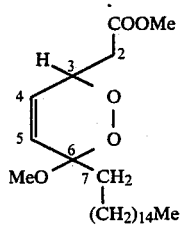

has been isolated from sponge of the genus *Chondrilla* which is distributed on the Great Barrier Reef. Isolation of Chondrillin is reported by R. J. Wells in "A Novel Peroxyketal From a Sponge", Tetrahedron Letters No. 30 pp. 2637–2638, Pergamon Press (1976). No bioactivity is reported for Chondrillin in this publication.

It has now been found that certain cylic peroxides compositions derived from extracts of the marine sponge, *Plakortis lita* possess useful antitumor activity.

SUMMARY OF THE INVENTION

It is therefore an object of the invention to provide novel compositions which are useful as antitumor agents and a process for producing such novel antitumor compositions.

Additional objects and advantages of the invention will be set forth, in part, in the description which follows and in part will be obvious from this description, or may be learned by the practice of the invention. The objects an advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the general formula (I)

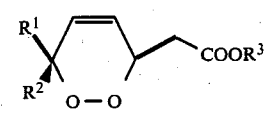

wherein Rhu 1 is hydrogen or an alkyl or alkenyl group of from 1 to 20 carbon atoms; $R^2$ is hydrogen or an alkyl or alkoxy groups of from 1 to 10 carbon atom; and $R^3$ is hydrogen or an alkyl group of from 1 to 10 carbon atoms.

In preferred embodiments of the invention, the composition is substantially pure and $R^1$ is an alkyl or alkenyl group of from 3–15 carbon atoms; $R^2$ is a lower alkyl or alkoxy group of from 1 to 5 carbon atoms; and $R^3$ is a lower alkyl group of from 1 to 5 carbon atoms or a hydrogen atom.

In more preferred embodiments of the invention, the invention comprises compositions of the formulae (II-V):

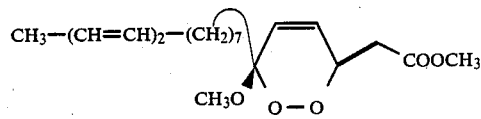

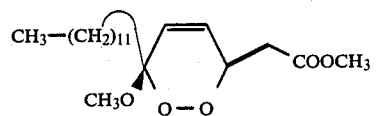

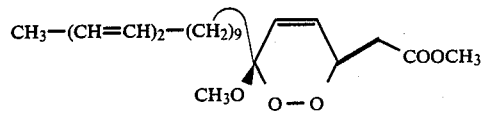

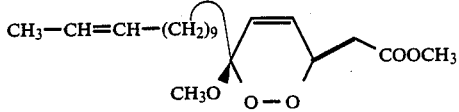

As embodied and fully described herein the invention also comprises an antitumor composition comprising, as active ingredient, an effective antitumor amount of one or more compositions according to formulae I-V and a non-toxic pharmaceutically acceptable carrier or diluent.

As embodied and fully described herein, the invention also comprises a process to produce the compounds of formulae I-V. The process comprises the steps of collecting marine sponge *Plakortis lita;* contacting the sponge with a suitable organic solvent; obtaining an oily extract thereof; and isolating a compound according to formulae I-V from the extract In preferred embodiments of the invention the suitable organic solvent is selected from the group consisting of acetone, methyl ethyl ketone, ethyl acetate, methanol, ethanol, and methyl isobutyl ketone.

As embodied and fully described herein, the invention further comprises a method for inhibiting tumors in a host and a therapeutic method for treating cancerous cachexia comprising contacting a tumor with an effective antitumor amount of one or more compositions of formulae I-V.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compositions of the general formulae (I):

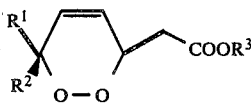

wherein $R^1$ is hydrogen or an alkyl or alkenyl group having from 1 to 20 carbon atoms; $R^2$ is hydrogen or an alkyl or alkoxy group having from 1 to 10 carbon atoms; and $R^3$ is hydrogen or an alkyl group of from 1 to 10 carbon atoms In preferred embodiments of the invention, the composition is substantially pure and $R^1$ is an alkyl or alkenyl group of 3-15 carbon atoms; $R^2$ is an alkyl or alkoxy group of from 1 to 5 carbon atoms; and $R^3$ is an alkyl group of from 1 to 5 carbon atoms or a hydrogen atom.

In more preferred embodiments of the invention, the invention comprises compositions of the formulae (II-V):

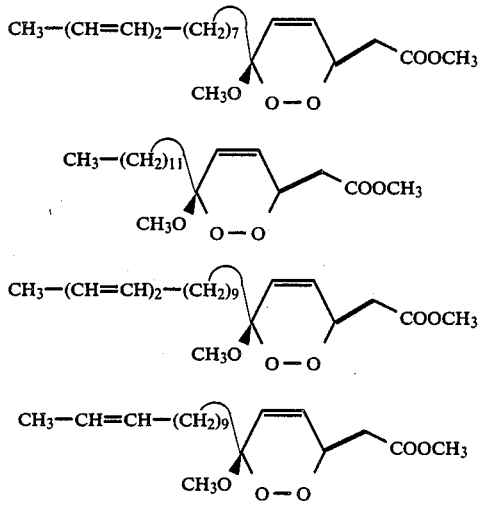

In accordance with the invention, an antitumor composition is provided comprising as active ingredient an effective antitumor amount of one or more of the compositions described above and identified by formulae I-V in a non-toxic pharmaceutically acceptable carrier or diluent. While effective amounts may vary, as conditions in which the antitumor compositions are used vary, a minimal dosage required for activity is generally between 0.01 and 100 micrograms against $10^5$ tumor cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of one or more compositions according to formulae I-VI. The effectiveness of the compositions of the invention for inhibiting tumors indicates their usefulness for controlling tumors in hosts including mammals and for treating cancerous cachexia.

In accordance with the invention, a process to produce a compound according to formulae I-V comprises the steps of: collecting marine sponge *Plakortis lita;* contacting the sponge with a suitable organic solvent; obtaining an oily extract thereof; and isolating a compound according to formulae I-V.

A detailed description and explanation of a preferred embodiment of the process of the invention to produce the compound according to formulas I-VI is as follows: marine sponge *Plakortis lita*, is collected in Onna, Okinawa. The marine sponge is freeze-dried and then contacted with ethyl acetate and homogenized in a mortar or blender. The ethyl acetate extract is concentrated by evaporation to give an oily organic residue. The residue is grossly separated into four fractions on a silca gel column eluted with 5:1, heptane ethyl acetate. The second fraction is then separated into an additional four subfractions. Compositions according to the invention are isolated from the second subfraction by countercurrent chromatographic techniques using an eluent system of 5:1:4, heptane: $CH_2Cl_2$: $CH_3CN$.

While ethyl acetate is the presently preferred choice for the extracting solvent, other suitable solvents may be substituted. A suitable solvent should be capable of extracting a compound according to any one of formulae I-V from other components of the marine sponge. Suitable first solvents which may be substituted for ethyl acetate include, but are not limited to, the following organic solvents methyl ethyl ketone; acetone; methanol; ethanol; and methyl isobutyl ketone Any suitable fractionation and isolation techniques may be utilized in accordance with the process of the invention. Suitable fractionation techniques include various chromotography techniques such as, high pressure liquid chromatography (HPLC) with a suitable column as would be known to those skilled in the art (e.g., silica gel column eluted with suitable eluents such as 5:1, heptane: ethyl acetate. Countercurrent chromatography techniques are also useful for isolating compositions of the invention. While examples of suitable eluents systems were described above, different eluents combinations and ratios thereof may be used in the invention as would be known to those skilled in the art.

EXAMPLES

The invention will now be illustrated by examples The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose method of preparation are not indicated are commercially available from sources known to the art such as chemical supply houses.

EXAMPLES 1-5

Antitumor Cyclic Peroxides were prepared from the Sponge *Plakortis lita* according to the following procedures.

Extraction and Separation

A sample of sponge *Plakortis lita* was collected at Onna, Okinawa and freeze-dried. 416 gms. dry weight of the sponge was extracted with ethyl acetate to give 20 gms of oil. The oil was separated on a silica gel column (5:1 heptane-ethyl acetate) into four fractions. The second fraction (3.8 gms) was again separated on the same chromatographic system into four subfractions. The second subfraction was then separated by countercurrent chromatography using a solvent system of 5:1:4, heptane-$CH_2Cl_2$-$CH_3CN$ (upper mobile phase). Repeated HPLC separation of each of the mobile phase fractions on an Altex ODS column ($CH_3CN$—$H_2O$) and/or LiChrosorb Si-60 column (heptane-EtOAc) gave five pure compounds (Examples 1-5). Table 1 shows the yields and melting points of these compounds. A detailed description of these compositions follows Table 1.

TABLE 1

Yields and Properties of cyclic peroxides

| Composition No. | Yield (mg) | MP (°C.) |
| --- | --- | --- |
| Example 1 | 800 | 31.5 |
| Example 2 | 10 | 38–39 |
| Example 3 | 14 | 49 |
| Example 4 | 4 | 47.5 |
| Example 5 | 7 | 37.5 |

EXAMPLE 1

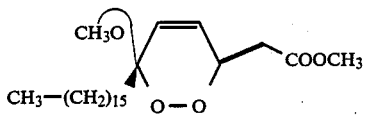

Compositon 1 as obtained as white solid, mp 31.5° C., $[\alpha]_d +38.5°$, and identified as known cyclic peroxide chondrillin, first isolated from the sponge *Chondrilla* sp. [R. J. Wells, *Tetrahedron Lett.*, 2637 (1976)]. It showed the following spectral properties: IR (KBr) 2910, 1735, 1462, 1435, 1248, 1160, 1142, 1127, 1055, and 982 $cm^{-1}$; $^1$H NMR (CDCl$_3$)$\delta$0.88 (3H, t, J=6.7 Hz), 1.25 (brs), 1.63 (2H, m), 2.62 (1H, dd, J=5.2, 16.1 Hz), 2.93 (1H, dd, J=8.1, 16.1 Hz), 3.40 (3H, s), 3.73 (3H, s), 4.78 (1H, m), 5.85 (1H, dd, J=1.8, 10,3 Hz), 6.18 (1H, dd, J=4.3, 10.2 Hz); $^{13}$C NMR (CDCl$_3$) $\delta$14.07q, 22.65t, 23.45t, 29.34t, 29.52t, 29.65 (t, 9C), 31.90t, 34.29t, 37.18, 50.69q, 51.90q, 73.66d, 100.47s, 126.43d, 129.20d, 170.83s; EIMS m/c 380 ($M^+$−$O_2$), 321, 293, 267, 183, 123, 113, and 43.

EXAMPLE 2

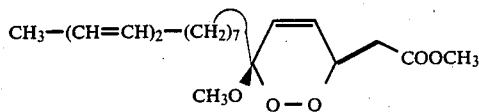

Composition 2 was obtained as a white solid mp 38–39° C., and has a Molecular formula of $C_{20}H_{32}O_5$. which was secured by high resolution mass measurement at ($M^+$−$O_2$) peak (m/z 320.2352, calcd for $C_{20}H_{32}O_3$: 320.2351). IR (film) 3015, 2922, 2852, 1740, 1460 (sh), 1433, 1389, 1356, 1270, 1245, 1190, 1164, 1132, 1110, 1062, 981, 950 (sh), and 740 $cm^{-1}$; $^1$NMR (CDCl$_3$)$\delta$1.26 (6H, brs), 1.34 (4H, m), 1.65 (2H, m), 1.73 (3H, d, J=6.5 Hz), 2.03 (2H, m), 2.51 (1H, dd, J=6.5, 16.1 Hz), 2.62 (1H, dd, J=7.5, 16.2 Hz), 3.39 (3H, s) 3.72 (3H, s), 5.01 (1H, dddd, J=1.5, 2.2, 6.5, 7.5 Hz), 5.56 (2H, m), 5.85 (1H, dd, J=2.2, 10.2 Hz), 6.00 (2H, m), and 6.12 (1H, dd, J=1.5, 10.2 Hz); $^{13}$C NMR (CDCl$_3$)$\delta$17.96, 23.23, 29.02, 29.26, 29.36, 29.66, 32.49, 34.81, 36.34, 51.29, 52.03, 73.48, 101.08, 126.67, 126.93, 130.25, 130.39, 131.71, 132.08, and 170.00; EIMS m/z 320, 304, 288, 261, 247, 233, 183, 123, 113, 95, and 81.

EXAMPLE 3

Composition 3 was obtained as a white solid, mp 49° C.; IR (film) 2950, 2918, 2846, 1737, 1458, 1438, 1395, 1370, 1275, 1230, 1193, 1160, 1145, 1069, 985, 955, 920, 873, 759, 716, and 699 $cm^{-1}$; $^1$H NMR (CDCl$_3$)$\delta$0.87 (3H, t), 1.15–1.4 (20H, brs), 1.66 (2H, m), 2.52 (1H, dd, 6.5, 16.1 Hz), 2.62 (1H, dd, J=7.5, 16.1 Hz), 3.39 (3H, s), 3.72 (3H, s), 5.01 (1H, brt, J=7.2 Hz), 5.86 (1H, dd, J=1.9, 10.0 Hz), and 6.12 (1H, brd. J=10.3 Hz); EIMS m/z 324, 265, 237, 211, 183, 170, 123, 113, 111, 109, 97, 83, and 43.

EXAMPLE 4

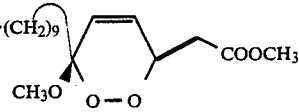

Composition 4 was obtained as a white solid. mp 47.5° C.; IR (film) 3057, 3020, 2955, 2918, 2880, 2848, 1737, 1464, 1436, 1392, 1375, 1315, 1279, 1227, 1193, 1176, 1162, 1144, 1102, 1069, 978, 955, 918, 862, 834, 757, 718, and 700 $cm^{-1}$, $^1$H, NMR (CDCl$_3$)$\delta$1.25 (brs), 1.33 (m), 1.64 (m), 1.72 (3H, d, J=6.4 Hz), 2.03 (2H, m), 2.51 (1H, dd, J=6.6, 16.0 Hz), 2.61 (1H, dd, J=7.5, 16.0 Hz), 3.38 (3H, s), 3.72(3H, s) 5.00 (1H, dddd, J=1.5, 2.1, 6.6, 7.5 Hz), 5.55 (2H, m), 5.84 (1H, dd, J=2.1, 10.3 Hz), 5.99 (2H, m), and 6.11 (1H, dd, J=1.5, 10.3 Hz); $^{13}$C NMR (CDCl$_3$)$\delta$17.95, 23.24t, 29.14t, 29.42t, 29.71t, 32.52t, 34.84t, 36.35t, 51.28, 52.02, 73.47, 101.08s, 126.61, 126.95, 130.21, 130.37, 131.73, 132.18, and 169,98s; EIMS m/z 348, 289, 221, 183, 171, 155, 147, 123, 113, 109, 107, 97, 95, 81, 79, and 67.

EXAMPLE 5

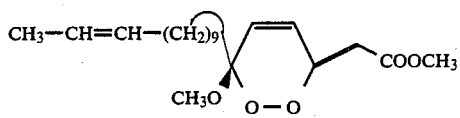

Composition 5 was obtained as a white solid, mp 37.5° C.; IR (film) 3020 (sh), 2915, 2845, 1735, 1450 (sh), 1435, 1390, 1375, 1313, 1277, 1225, 1191, 1160, 1100, 1067, 1029, 997, 984, 958, 922, 870, 858, 833, 816, 756, 718, and 699 cm$^{-1}$; $^1$H NMR (CDCl$_3$)δ126 (brs), 1.32 (m), 1.64 (m), 1.96 (m) 2.52 (1H, dd, J=6.6, 16.0 Hz), 2.62 (1H, dd J=7.5, 16.0 Hz), 3.40 (3H, s), 3173 (3H, s), 5.02 (1H, m) 5.42 (2H, m), 5.85 (1H, dd), and 6.12 (1H, dd); $^{13}$C NMR (CDCl$_3$)δ23.29, 29.18, 29.43, 29.63, 29.76, 32.61, 34.84, 36.38, 51.30, 52.06, 73.51, 101.11, 124.55, 126.97, 130.40, 131.69, and 170.00; EIMS m/z 322, 263, 238, 183, 170, 153, 123, 113, 111, and 55.

Composition 1 is identified as the known compound chondrillin. Compositions 2-5 are structurally distinct from chondrillin because of their own unique substituent groups and the fact that they are epimers of chondrillin in regard to the stereochemical orientation of their substituent groups.

ANTITUMOR ACTIVITIES OF THE COMPOUNDS OF THE INVENTION

The following assay method was utilized to illustrate the antitumor effectiveness of the compositions of Formulae II - VI corresponding to compositions 2-5 of the examples. Data is also provided for the chondrillin composition (1) which has also been isolated according to the process of the invention.

b 388 MOUSE LEUKEMIA CELL CYTOXICITY ASSAY 24-WELL PLATE SCREENING ASSAY AND TUBE ASSAY PROTOCOL
MATERIALS UTILIZED
Media—Dulbeccos with glucose and pyruvate (Biologos, Inc) with 10% horse serum, (Biologos, Inc) and 1.0 ug/ml gentamicin (Gibco).

Cells - P-388 mouse leukemia cells (American Type Culture Collection) in media at a concentration of 5×10$^4$ W cells/ml Sterile 24-well culture plates (Nunc) for screening or 12×75 mm glass culture tubes (Becton-Dickinson) for tube assay. Microdispenser with 1 to 5 ul increments (Drummond Scientific Co. Broomall PA).

Finnpipette with 5 to 50 μl increments and Finnpipette with 50 to 200 μl increments.

PROCEDURE
1. A sample of the composition to be assayed is added to each well or tube in an amount of from 200 ug/ml and 100 ug/ml for screening. For DDC of known active compounds use log concentrations from 100 ug/ml to 0.01 ug/ml for range-finding assay; when range has been determined, use five concentrations between highest and lowest active concentrations.
2. Add 2.0 ml of 5×10$^4$ cell suspension in media to each well or tube. Tubes are loosely covered with parafilm.
3 Incubate in 5% CO$_2$ incubator 48 hours.
4. Visually read plates with inverted microscope, comparing with solvent control. Assign activity as follows:
0=90-100% of control growth
1+=75-89% of control growth
2+=50-74% of control growth
3+=25-49% of control growth
4+=25of control growth
Repeat all positive samples using tube assay.
5. For Tube assays—Mix tube well on vortex and remove 0.5 ml aliquot and add to 9.5 ml of diluent fluid (Isoton - Coulter) in Accuvette (Coulter) and mix well by inversion immediately before counting, taking care not to produce excessive bubbles. Count on Coulter Counter (Counter is set to count 0.5 ml of the solution; therefore counts may be converted to cell/ml in original assay tube by multiplying count by 40.

Positive control—Vinblastine or Vincristine in aqueous solution.

Final Conc. of Vinblastine or Vincristine control (use 2 μl/assay)

| Solution Conc. | Amt added | Final conc. in test |
|---|---|---|
| 5 mg/ml | 2 ul | 5 ug/ml |
| 1 mg/ml | 2 ul | 1 ug/ml |
| 0.1 mg/ml | 2 ul | 0.1 ug/ml |
| 0.05 mg/ml | 2 ul | 0.05 ug/ml |

Notes:
1. For solvents other than water, allow solvent to evaporate from tube or well in hood.
2. Chloroform and butanol cannot be used in the plastic 24-well plates - use glass tubes.

Always run a solvent control in duplicate in the last two wells of each plate or four tubes for each rack of 72 or less tubes. Also run four wells or tubes with media and cells only per run of plates or tubes. When using volumes of aqueous solutions greater than 200 μl, dry sample and bring up to desired concentration in media.

The results of the above assay are summarized below in Table 2. Compositions 1-5 of formulae I/1; II/2; III/3; IV/4; and V/5 are cytotoxic in vitro against P-388 murine leukemia cells.

TABLE 2

| Antitumor Assay Results | |
|---|---|
| Composition Formula/Example | P388 IC$_{50}$ (ug/ml) Inhibiting concentration 50% of cell growth |
| I/1 | 5 |
| II/2 | 0.05 |
| III/3 | 0.05 |
| IV/4 | 0.1 |
| V/5 | 0.1 |

Table 2 shows that compositions II/2 and III/3 show the greatest antitumor activity of the compositions tested. Compositions II/2 and III/3 are shown to be effective in inhibiting 50% of cell growth of P388 mouse leukemia cells at 1% the concentration required for inhibition by chondrillin (composition 1). Similarly, compositions IV/4 and V/5 are also shown to be effective at inhibiting the growth of P388 mouse leukemia cells at 2% the concentration required for inhibition by chondrillin (composition 1).

It is apparent from the in vitro testing that the compositions of the invention, are effective for inhibiting or destroying tumors and therefore controlling diseases caused by or related to such tumors such as cancerous cachexia in fulfillment of the objects of the invention.

The scope of the present invention is not limited by the description, examples, and suggested uses herein and modifications can be made without departing from the spirit of the invention. For example, it may be noted that other derivatives of the compositions of examples 1-5 such as hydroxy or halogenated derivatives may possess antitumor activity analogous to those preferred embodiments described above. Further, the compositions described herein may have other useful applications such as, for example, analgesic applications. Application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A compound selected from the group consisting of:

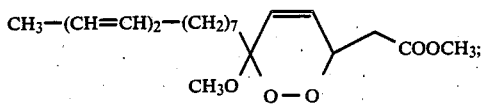

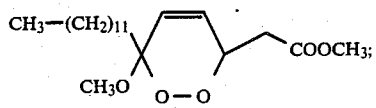

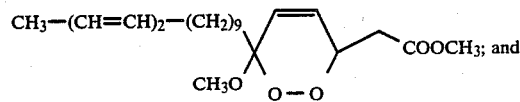

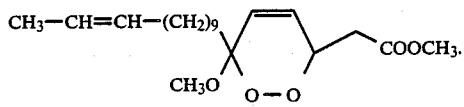

2. A compound according to claim 1 of the formula:

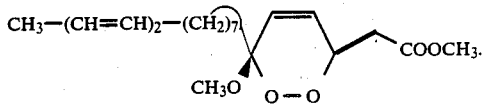

3. A compound according to claim 1 of the formula:

4. A compound according to claim 1 of the formula:

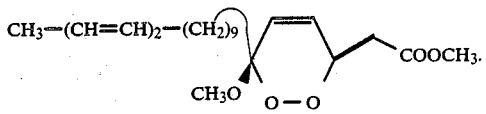

5. A compound according to claim 1 of the formula:

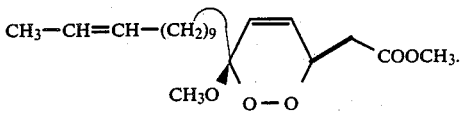

6. The compound according to claim 1 wherein said compound is substantially pure.

7. An antitumor composition comprising, as active ingredient, an effective antitumor amount of one or more of the compounds of claim 1 and a non-toxic pharmaceutically acceptable carrier or diluent.

* * * * *